US012644881B2

(12) United States Patent (10) Patent No.: US 12,644,881 B2
Zhong et al. (45) Date of Patent: Jun. 2, 2026

(54) ALCOHOL TEST METHOD AND APPARATUS

(71) Applicant: SHENZHEN EVERBEST MACHINERY INDUSTRY CO., LTD., Shenzhen (CN)

(72) Inventors: Lijun Zhong, Shenzhen (CN); Lianghua Song, Shenzhen (CN)

(73) Assignee: SHENZHEN EVERBEST MACHINERY INDUSTRY CO., LTD., Shenzhen (CN)

( * ) Notice: Subject to any disclaimer, the term of this patent is extended or adjusted under 35 U.S.C. 154(b) by 361 days.

(21) Appl. No.: 18/035,515

(22) PCT Filed: Dec. 4, 2020

(86) PCT No.: PCT/CN2020/134086
§ 371 (c)(1),
(2) Date: May 5, 2023

(87) PCT Pub. No.: WO2022/116208
PCT Pub. Date: Jun. 9, 2022

(65) Prior Publication Data
US 2024/0011972 A1 Jan. 11, 2024

(51) Int. Cl.
*G01N 33/98* (2006.01)
*G01N 33/497* (2006.01)
(52) U.S. Cl.
CPC ................................. *G01N 33/4972* (2013.01)

(58) Field of Classification Search
CPC ........................... G01N 33/4972; G01N 33/98
USPC ..................................................... 73/1.06, 23.3
See application file for complete search history.

(56) References Cited

U.S. PATENT DOCUMENTS

| | | | | | |
|---|---|---|---|---|---|
| 5,443,794 | A | * | 8/1995 | Williams | ........... G01N 33/4972 73/23.3 |
| 10,222,367 | B2 | * | 3/2019 | Tschuncky | ......... G01N 33/0006 |
| 2015/0335265 | A1 | * | 11/2015 | Evans | ................... B60W 40/08 701/113 |

FOREIGN PATENT DOCUMENTS

| | | |
|---|---|---|
| CN | 107618370 A | 1/2018 |
| CN | 108152345 A | 6/2018 |

OTHER PUBLICATIONS

International Search Report of PCT Patent Application No. PCT/CN2020/134086 issued on Aug. 30, 2021.

\* cited by examiner

*Primary Examiner* — Robert R Raevis

(57) ABSTRACT

An alcohol test method and apparatus. The alcohol test method comprises: receiving gas exhaled by a testee from a gas channel (S101); measuring an alcohol content in the gas according to the gas exhaled by the testee from the gas channel (S102); obtaining a gas alcohol concentration value according to the measured alcohol content in the gas (S103); and calculating an output alcohol concentration value according to the gas alcohol concentration value (S104). By means of a method for conveniently measuring the alcohol concentration, the alcohol concentration of the gas exhaled by the testee can be rapidly measured.

10 Claims, 6 Drawing Sheets

Alcohol test apparatus

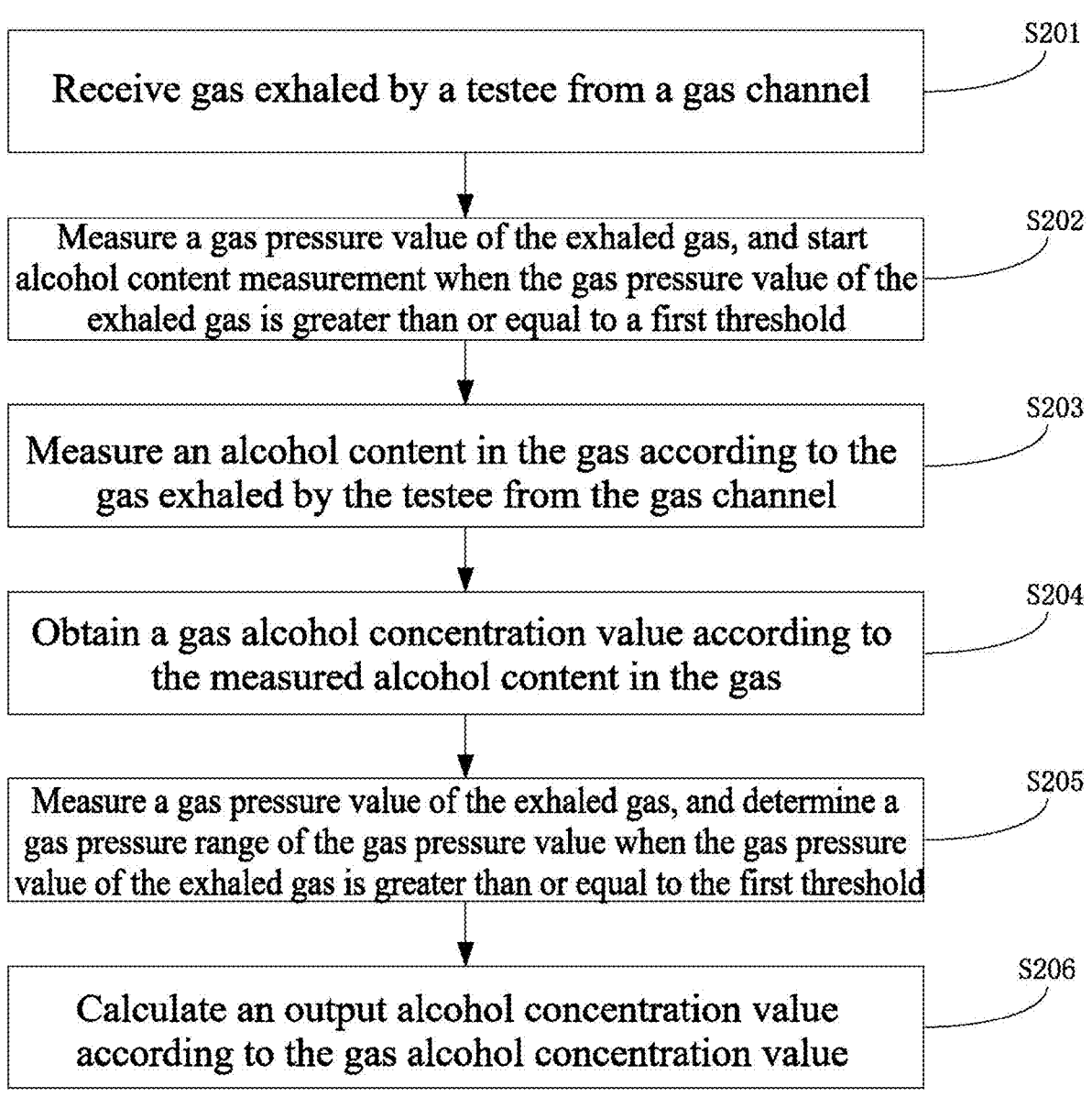

Receive gas exhaled by a testee from a gas channel

S201

Measure a gas pressure value of the exhaled gas, and start alcohol content measurement when the gas pressure value of the exhaled gas is greater than or equal to a first threshold

S202

Measure an alcohol content in the gas according to the gas exhaled by the testee from the gas channel

S203

Obtain a gas alcohol concentration value according to the measured alcohol content in the gas

S204

Measure a gas pressure value of the exhaled gas, and determine a gas pressure range of the gas pressure value when the gas pressure value of the exhaled gas is greater than or equal to the first threshold

S205

Calculate an output alcohol concentration value according to the gas alcohol concentration value

Alcohol test apparatus

Alcohol test apparatus

Receiving unit — 601

Starting unit — 602

Measurement unit — 603

Concentration calculation unit — 604

Gas pressure measurement starting unit — 605

Output unit — 606

Output unit — 607

604

Concentration correction unit — 701

Direct concentration calculation unit — 702

ALCOHOL TEST METHOD AND APPARATUS

TECHNICAL FIELD

The present application relates to the technical field of alcohol test, and in particular to an alcohol test method and apparatus.

BACKGROUND ART

Since the punishment for drunk driving came into effect, drunk driving cases have become one of the most common types of cases handled by the judiciary. The traffic police usually uses an exhaled gas alcohol content tester as a rapid test tool for drunk driving in the fight against drunk driving. Rapid alcohol content test can effectively avoid the occurrence of traffic accidents, and can also be widely used in some high-risk areas or areas where work after drinking is prohibited.

With the improvement of residents' living standards, there are inevitably more and more alcohol consumptions, and the nascent industry of designated driving is also developing. However, the high cost of designated driving sometimes makes drinkers take a risk, and some will choose to drive by themselves after a break. In this case, an alcohol test device is needed to rapidly measure the alcohol concentration. A conventional alcohol test device is large in size and not easy to carry.

TECHNICAL PROBLEM

An objective of the embodiments of the present application is to provide an alcohol test method and apparatus, aiming at providing a method for conveniently measuring an alcohol concentration to rapidly measure the alcohol concentration in the gas exhaled by a testee for test.

TECHNICAL SOLUTIONS

The embodiments of the present application are implemented by an alcohol test method, comprising:

receiving gas exhaled by a testee from a gas channel;

measuring an alcohol content in the gas according to the gas exhaled by the testee from the gas channel;

obtaining a gas alcohol concentration value according to the measured alcohol content in the gas; and calculating an output alcohol concentration value according to the gas alcohol concentration value.

Further, the method further comprises, after receiving gas exhaled by a testee from a gas channel, measuring a gas pressure value of the exhaled gas, and starting alcohol content measurement when the gas pressure value of the exhaled gas is greater than or equal to a first threshold.

Further, the method further comprises, after obtaining a gas alcohol concentration value according to the measured alcohol content in the gas, measuring a gas pressure value of the exhaled gas, and determining a gas pressure range of the gas pressure value when the gas pressure value of the exhaled gas is greater than or equal to a first threshold.

Further, calculating an output alcohol concentration value according to the gas alcohol concentration value specifically comprises:

correcting the gas alcohol concentration value when the gas pressure value of the exhaled gas is greater than or equal to the first threshold and less than or equal to a second threshold, and outputting the corrected value as the alcohol concentration value; and outputting the gas alcohol concentration value as the alcohol concentration value when the gas pressure value of the exhaled gas is greater than the second threshold.

Further, a calculation formula for correcting the gas alcohol concentration value is:

$$G_D = k * \left(1 + \frac{p_2 - p_x}{p_2 - p_1}\right) * G_X;$$

where $G_D$ is the corrected alcohol concentration, $G_x$ is the alcohol concentration, P2 is the second threshold, P1 is the first threshold, Px is the gas pressure value of the exhaled gas, and k is a measurement uncertainty coefficient.

Another objective of the embodiments of the present application is to provide an alcohol test apparatus, comprising:

a receiving unit configured to receive gas exhaled by a testee from a gas channel;

a measurement unit configured to measure an alcohol content in the gas according to the gas exhaled by the testee from the gas channel;

a concentration calculation unit configured to obtain a gas alcohol concentration value according to the measured alcohol content in the gas; and an output unit configured to calculate an output alcohol concentration value according to the gas alcohol concentration value.

Further, the apparatus further comprises:

a starting unit configured to measure a gas pressure value of the exhaled gas, and start alcohol content measurement when the gas pressure value of the exhaled gas is greater than or equal to a first threshold.

Further, the apparatus further comprises:

a gas pressure measurement starting unit configured to measure a gas pressure value of the exhaled gas and determine a gas pressure range of the gas pressure value when the gas pressure value of the exhaled gas is greater than or equal to the first threshold.

Further, the concentration calculation unit comprises:

a concentration correction unit configured to correct the gas alcohol concentration value when the gas pressure value of the exhaled gas is greater than or equal to the first threshold and less than or equal to a second threshold, and output the corrected value as the alcohol concentration value; and a direct concentration calculation unit configured to output the gas alcohol concentration value as the alcohol concentration value when the gas pressure value of the exhaled gas is greater than the second threshold.

Further, the apparatus further comprises:

a correction calculation unit configured to correct and calculate the gas alcohol concentration value by a calculation formula of $$G_D = k * \left(1 + \frac{p_2 - p_x}{p_2 - p_1}\right) * G_X;$$

where $G_D$ is the corrected alcohol concentration, $G_x$ is the alcohol concentration, P2 is the second threshold, P1 is the first threshold, Px is the gas pressure value of the exhaled gas, and k is a measurement uncertainty coefficient.

BENEFICIAL EFFECTS

According to the embodiments of the present application, the alcohol test device is used to receive the gas exhaled by the testee from the gas channel, obtain the relevant data of the gas, and finally calculate the alcohol concentration value in the body (blood) of the testee. Thus, a rapid and convenient alcohol test method is provided to, when a user needs to accurately determine the alcohol value after drinking, help the user accurately determine the alcohol consumption to make a correct determination. In particular, an alcohol sensor that can be applied to a wearable device is used. The sensor can be embedded in a small smart device or terminal device to read the data, remind the user of the current alcohol concentration according to the data, and send an alarm.

BRIEF DESCRIPTION OF THE DRAWINGS

In order to explain the technical solutions in the embodiments of the present application more clearly, the drawings used in the embodiments or the description of the prior art will be briefly introduced below. Obviously, the drawings in the description below are only some embodiments of the present application, and for those of ordinary skill in the art, other drawings can be obtained based on these drawings without involving any inventive effort.

FIG. 2 is a flowchart of implementation of an alcohol test method provided according to a second embodiment of the present application;

DETAILED DESCRIPTION OF EMBODIMENTS

In order to enable those skilled in the art to better understand the solution of the present application, the technical solutions in the embodiments of the present application will be clearly described below with reference to the accompanying drawings of the embodiments of the present application. Apparently, the embodiments described are merely some rather than all of the embodiments of the present application. On the basis of the embodiments of the present application, all other embodiments obtained by a person of ordinary skill in the art without involving any inventive effort shall fall within the scope of protection of the present application.

The terms "first", "second", "third", "fourth", etc. (if any) in the specification and the claims of the present application and the drawings mentioned above is intended to distinguish similar objects from each other, rather than describing a specific order or sequence. It should be understood that the terms used in this way are interchangeable where appropriate such that the embodiments described herein can be implemented in a sequence other than those illustrated or described herein. In addition, the terms "comprise" and "have" and any variations thereof are intended to cover a non-exclusive inclusion, for example, a process, a method, a system, a product or a device including a series of steps or units is not necessarily limited to the steps or units explicitly listed, but can include other steps or units that are not explicitly listed or inherent to the process, the method, the product or the device.

The implementation of the present application will be described in detail below in conjunction with the specific embodiments.

Embodiment I

Figure 1:
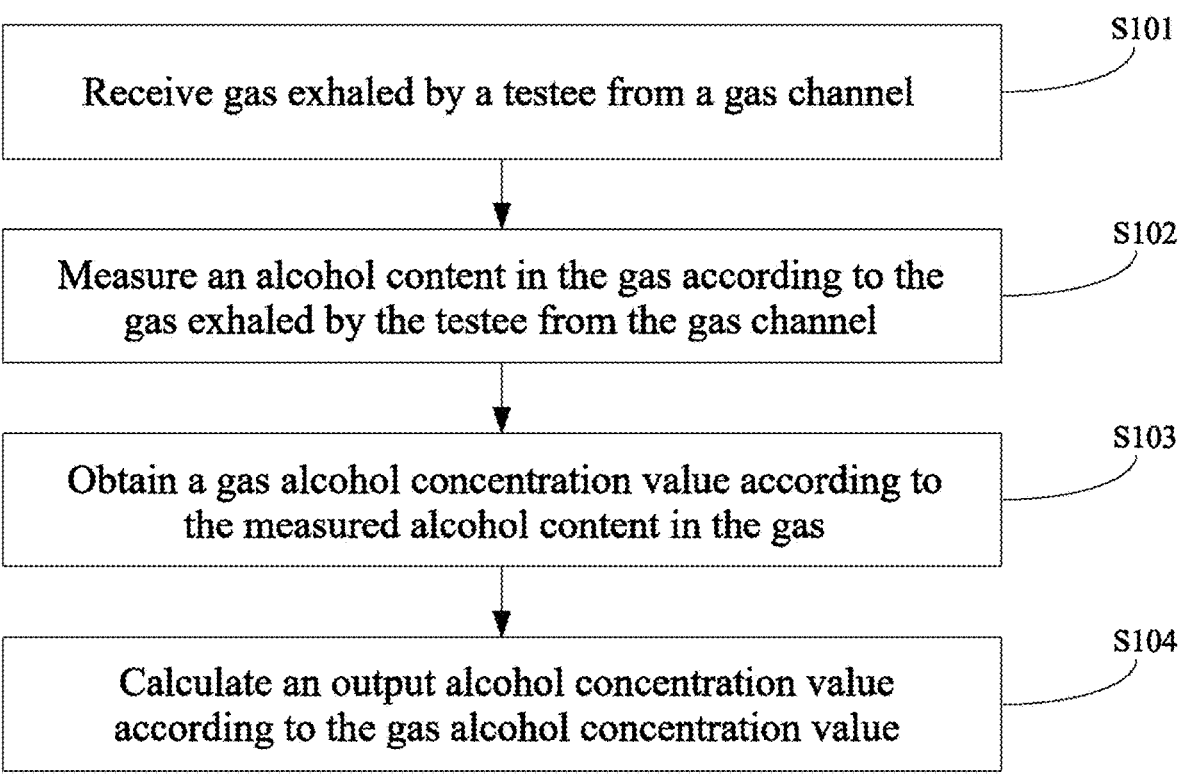
FIG. 1 is a flowchart of implementation of an alcohol test method provided according to a first embodiment of the present application.

FIG. 1 shows a process of implementation of an alcohol test method provided according to a first embodiment of the present application, which is described in detail as follows.

In step S101, gas exhaled by a testee from a gas channel is received.

In the specific implementation process, a gas inlet of a test device can receive the gas in the breath exhaled by the testee. Since the exhaled gas in the breath has a certain flow rate, the gas flow can rapidly enter the test device from the gas inlet of the test device, and the gas then enters the gas channel via the gas inlet and finally enters a measurement unit of the test device, realizing the function of receiving gas.

In step S102, an alcohol content in the gas is measured according to the gas exhaled by the testee from the gas channel.

In the specific implementation process, after the test device receives the exhaled gas, the test device can test the exhaled gas entering the gas channel, and measure the alcohol content in the body of the testee according to the measurement of the alcohol content in the gas.

In step S103, a gas alcohol concentration value is obtained according to the measured alcohol content in the gas.

In the specific implementation process, when the alcohol content value of the gas in the breath exhaled by the testee is obtained, the alcohol concentration value of the gas can be calculated according to the gas alcohol value. The gas alcohol value is an alcohol content value of the gas exhaled by the testee, and the gas alcohol concentration value is an alcohol content value in the body (blood) of the testee. Since there is a certain proportional numerical relationship between the alcohol content value during the human breathing process and the alcohol content value in the body (blood), the alcohol concentration value in the body (blood) of the testee can be calculated when the gas alcohol value is obtained.

In step S104, an output alcohol concentration value is calculated according to the gas alcohol concentration value.

In the specific implementation process, when the gas alcohol concentration value is obtained, it is necessary to correct the specific alcohol concentration value or convert the corresponding relationship according to the actual situation. Since the alcohol concentration value of the gas in the breath exhaled by the testee and the alcohol concentration value in the body (blood) of the testee have a corresponding relationship that needs to be corrected, the value needs to be corrected again, and the final alcohol concentration value can only be output after the correction.

According to the embodiment of the present application, an alcohol test method is provided. In the method, the alcohol test device is used to receive the gas exhaled by the testee from the gas channel, obtain the relevant data of the gas, and finally calculate the alcohol concentration value in the body (blood) of the testee. Thus, a rapid and convenient alcohol test method is provided to, when a user needs to accurately determine the alcohol value after drinking, receive and test the gas exhaled by the testee by means of the test device to rapidly obtain the alcohol value in the body (blood) of the testee, which helps the user accurately determine the alcohol consumption to make a correct determination.

Embodiment II

FIG. 2 shows a process of implementation of an alcohol test method provided according to a second embodiment of the present application, which is described in detail as follows.

In step S201, gas exhaled by a testee from a gas channel is received.

In the specific implementation process, a gas inlet of a test device can receive the gas in the breath exhaled by the testee. Since the exhaled gas in the breath has a certain flow rate, the gas flow can rapidly enter the test device from the gas inlet of the test device, and the gas then enters the gas channel via the gas inlet and finally enters a measurement unit of the test device, realizing the function of receiving gas.

In step S202, a gas pressure value of the exhaled gas is measured, and alcohol content measurement is started when the gas pressure value of the exhaled gas is greater than or equal to a first threshold.

In the specific implementation process, since the exhaled gas in the breath will enter air and be mixed with gas in the air, the gas flow rate will decrease during the mixing process, the lower the flow rate of the exhaled gas, the better it mixes with the gas in the air. When the exhaled gas in the breath is mixed with a large amount of the gas in the air due to too low flow rate of the exhaled gas or when the exhaled gas in the breath is too far away from the test device, the exhaled gas will be fully mixed with the gas in the air, which will eventually lead to serious deviations in the testing data. Therefore, in order to obtain accurate data, it is necessary to measure the gas pressure value of the exhaled gas, measure the gas pressure value of the gas exhaled into the test device, determine whether to start alcohol content measurement according to the gas pressure value, and start alcohol content measurement when the gas pressure value of the exhaled gas is greater than or equal to the set first threshold.

In step S203, an alcohol content in the gas is measured according to the gas exhaled by the testee from the gas channel.

In the specific implementation process, after the test device receives the exhaled gas, the test device can test the exhaled gas entering the gas channel, and measure the alcohol content in the body of the testee according to the measurement of the alcohol content in the gas.

In step S204, a gas alcohol concentration value is obtained according to the measured alcohol content in the gas.

In the specific implementation process, when the alcohol content value of the gas in the breath exhaled by the testee is obtained, the alcohol concentration value of the gas can be calculated according to the gas alcohol value. The gas alcohol value is an alcohol content value of the gas exhaled by the testee, and the gas alcohol concentration value is an alcohol content value in the body (blood) of the testee. Since there is a certain proportional numerical relationship between the alcohol content value during the human breathing process and the alcohol content value in the body (blood), the alcohol concentration value in the body (blood) of the testee can be calculated when the gas alcohol value is obtained.

In step S205, a gas pressure value of the exhaled gas is measured, and a gas pressure range of the gas pressure value is determined when the gas pressure value of the exhaled gas is greater than or equal to the first threshold.

In the specific implementation process, since the exhaled gas in the breath will enter air and be mixed with the gas in the air, the gas flow rate will decrease during the mixing process, the lower the flow rate of the exhaled gas, the better it mixes with the gas in the air. The exhaled gas in the breath at too low flow rate will be mixed with a large amount of the gas in the air, but the exhaled gas in the breath at a high flow rate may infer that the exhaled gas is in proximity and is difficult to mix with the gas in the air. Therefore, it is necessary to distinguish the gas at different flow rates from each other for accurate test. In this case, it is necessary to measure the gas pressure value of the exhaled gas, determine the gas pressure range of the gas pressure value when the gas pressure value of the exhaled gas is greater than or equal to the first threshold, and correct the value of the subsequent relevant data according to the measured gas pressure value.

In step S206, an output alcohol concentration value is calculated according to the gas alcohol concentration value.

Figure 3:
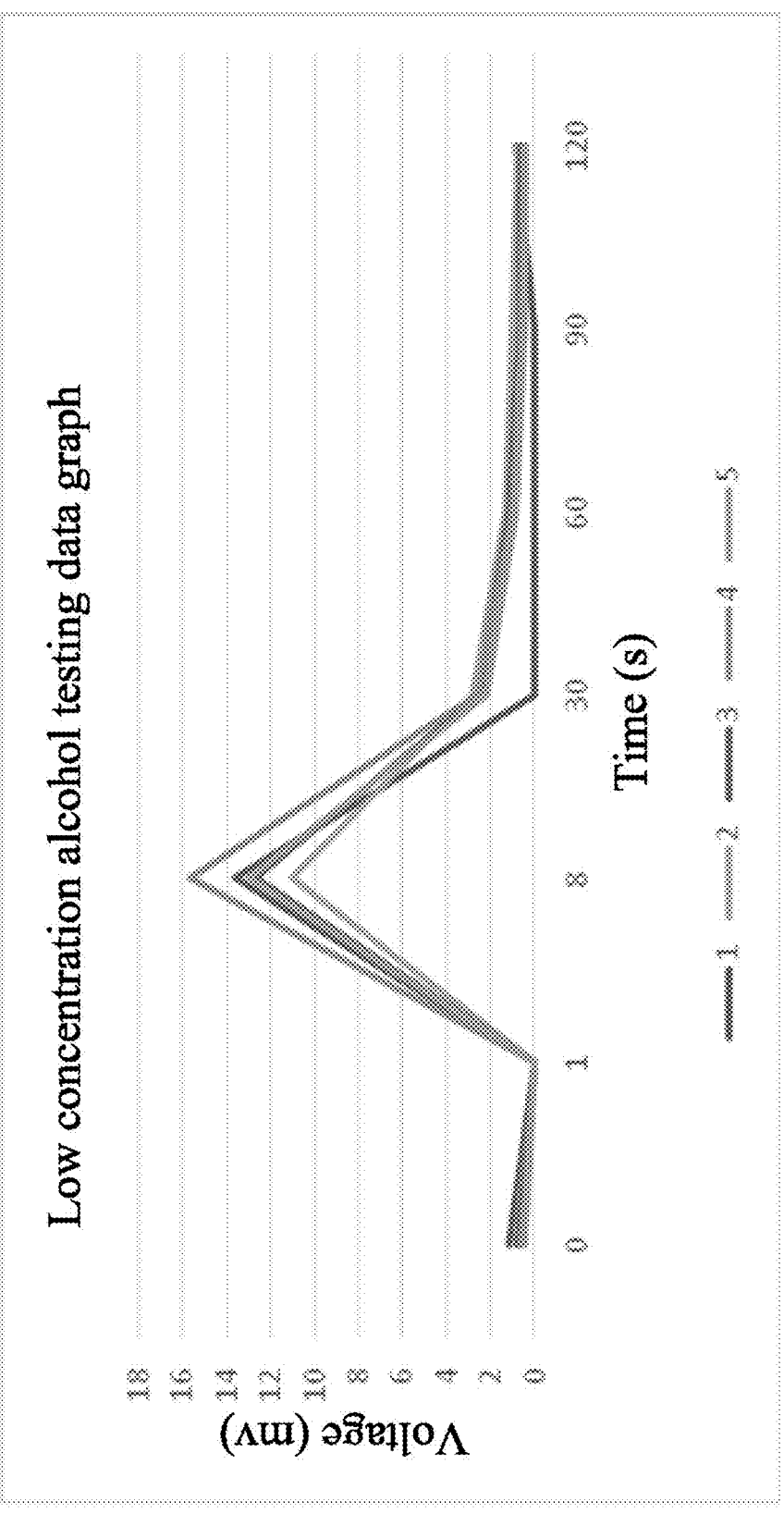
FIG. 3 shows the k value of low concentration alcohol testing data graph provided according to the second embodiment of the present application.
Figure 4:
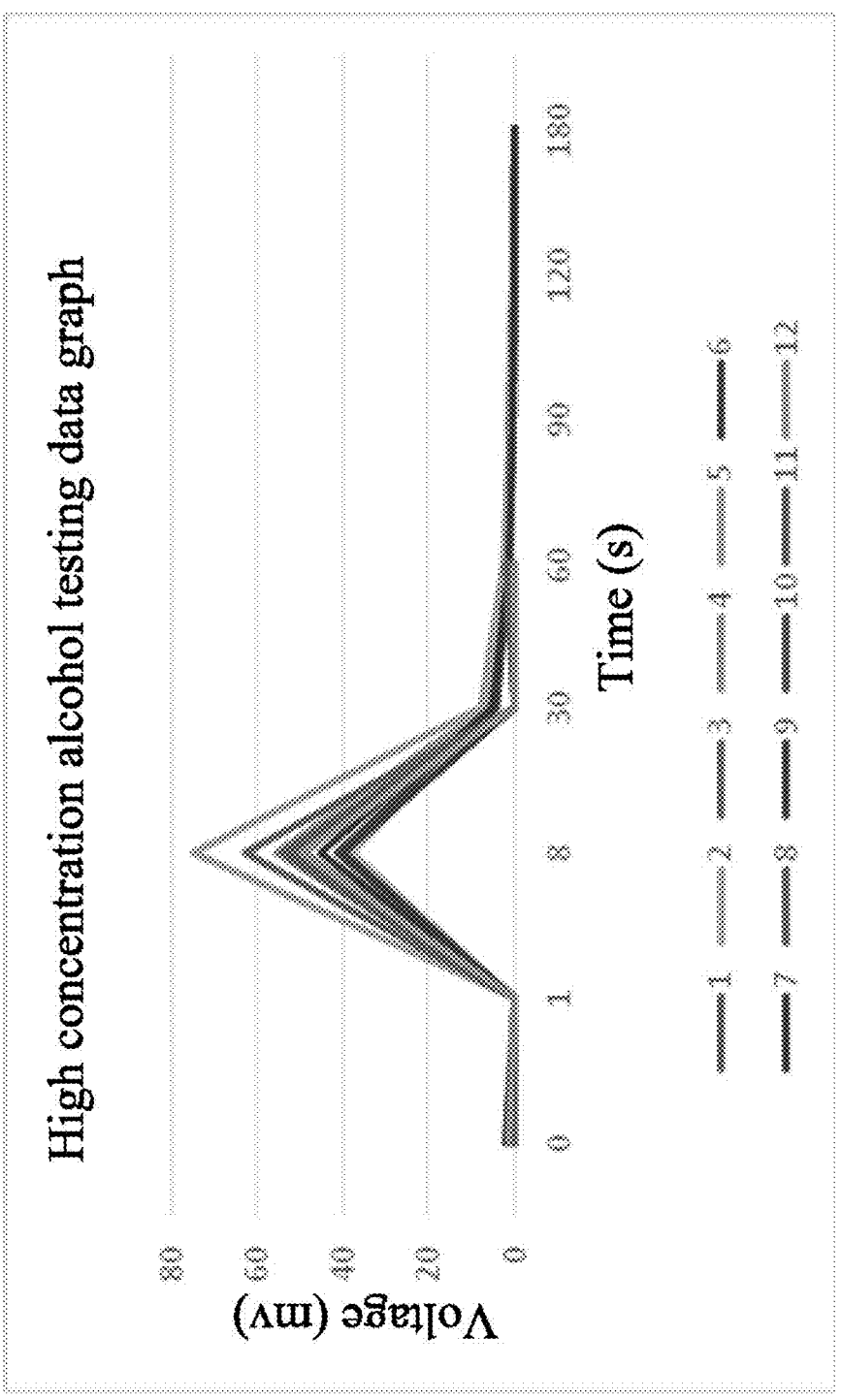
FIG. 4 shows the k value of high concentration alcohol testing data graph provided according to the second embodiment of the present application.

In the specific implementation process, when the gas alcohol concentration value is obtained, it is necessary to correct the specific alcohol concentration value or convert the corresponding relationship according to the actual situation. Since the alcohol concentration value of the gas in the breath exhaled by the testee and the alcohol concentration value in the body (blood) of the testee have a corresponding relationship that needs to be corrected, the value needs to be corrected again. After the gas pressure range of the gas pressure value is determined, the gas alcohol concentration value is corrected when the gas pressure value of the exhaled gas is greater than or equal to the first threshold and less than or equal to a second threshold, and the corrected value is output as the alcohol concentration value; and the gas alcohol concentration value is output as the alcohol concentration value when the gas pressure value of the exhaled gas is greater than the second threshold. A calculation formula for correcting the gas alcohol concentration value is:

$$G_D = k * \left(1 + \frac{p_2 - p_x}{p_2 - p_1}\right) * G_X;$$

where $G_D$ is the corrected alcohol concentration, $G_x$ is the alcohol concentration, P2 is the second threshold, P1 is the first threshold, Px is the gas pressure value of the exhaled gas. Preferably, the pressure value of the exhaled gas of P1 is between 150 Pa and 240 Pa, the pressure value of the exhaled gas of P2 is between 300 Pa and 500 Pa, and k is a measurement uncertainty coefficient. In the actual measurement, there will be certain uncertainty due to different sensors. The different curves marked by 1-5 or 1-12 in the figures represent different sample individuals. Through the experiment, it is found that there are large difference between different sample individuals, so that there will be some differences in the data calculated completely by using the formula. Thus, the k value coefficient is added, and the MCU will give different k values according to the actual sampled data during the sample preparation process to correct the entire algorithm curve. The setting of this uncertainty can be used to adjust the accuracy of the actual output. The schematic diagrams of k value are shown in FIGS. 3 and 4. FIG. 3 shows the k value of low concentration alcohol testing data graph, and FIG. 4 shows the k value of high concentration alcohol testing data graph. The data graphs of k value under different alcohol concentrations are shown. After correction, a more accurate final alcohol concentration value can be output.

According to the embodiment of the present application, an alcohol test method is provided. The alcohol test device is used to receive the gas exhaled by the testee from the gas channel, obtain the relevant data of the gas, and finally calculate the alcohol concentration value in the body (blood) of the testee. In order to obtain more accurate data, the test is only performed when the gas pressure reaches a certain value. In addition, in order to apply this test method to a small smart device or terminal device, it is also possible to measure the gas pressure without providing a mouthpiece and correct the data according to the gas pressure value, so that the hardware device for test can be a small smart device or terminal device without a mouthpiece. Thus, a rapid and convenient alcohol test method is provided to, when a user needs to accurately determine the alcohol value after drinking, receive and test the gas exhaled by the testee by means of the test device to rapidly obtain the alcohol value in the body (blood) of the testee, which helps the user accurately determine the alcohol consumption to make a correct determination.

Embodiment III

Figure 5:
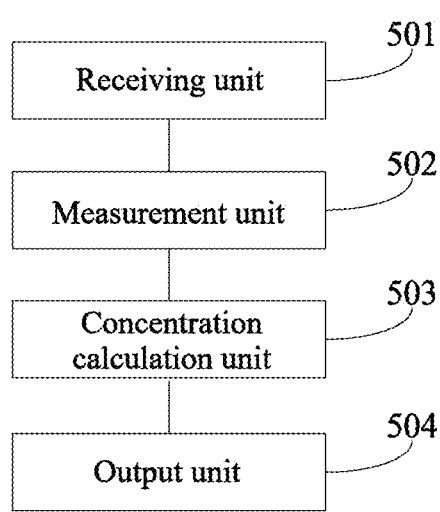
FIG. 5 is a structural view of an alcohol test apparatus provided according to a third embodiment of the present application.

FIG. 5 shows a structural view of an alcohol test apparatus provided according to a third embodiment of the present application, and, for ease of illustration, only shows the parts related to the embodiment of the present application.

A receiving unit 501 is configured to receive gas exhaled by a testee from a gas channel.

In the specific implementation process, a gas inlet of a test device can receive the gas in the breath exhaled by the testee. Since the exhaled gas in the breath has a certain flow rate, the gas flow can rapidly enter the test device from the gas inlet of the test device, and the gas then enters the gas channel via the gas inlet and finally enters a measurement unit of the test device, realizing the function of receiving gas.

A measurement unit 502 is configured to measure an alcohol content in the gas according to the gas exhaled by the testee from the gas channel.

In the specific implementation process, after the test device receives the exhaled gas, the test device can test the exhaled gas entering the gas channel, and measure the alcohol content in the body of the testee according to the measurement of the alcohol content in the gas.

A concentration calculation unit 503 is configured to obtain a gas alcohol concentration value according to the measured alcohol content in the gas.

In the specific implementation process, when the alcohol content value of the gas in the breath exhaled by the testee is obtained, the alcohol concentration value of the gas can be calculated according to the gas alcohol value. The gas alcohol value is an alcohol content value of the gas exhaled by the testee, and the gas alcohol concentration value is an alcohol content value in the body (blood) of the testee. Since there is a certain proportional numerical relationship between the alcohol content value during the human breathing process and the alcohol content value in the body (blood), the alcohol concentration value in the body (blood) of the testee can be calculated when the gas alcohol value is obtained.

An output unit 504 is configured to calculate an output alcohol concentration value according to the gas alcohol concentration value.

In the specific implementation process, when the gas alcohol concentration value is obtained, it is necessary to correct the specific alcohol concentration value or convert the corresponding relationship according to the actual situation. Since the alcohol concentration value of the gas in the breath exhaled by the testee and the alcohol concentration value in the body (blood) of the testee have a corresponding relationship that needs to be corrected, the value needs to be corrected again, and the final alcohol concentration value can only be output after the correction.

According to the embodiment of the present application, an alcohol test apparatus is provided. With the apparatus, the alcohol test device is used to receive the gas exhaled by the testee from the gas channel, obtain the relevant data of the gas, and finally calculate the alcohol concentration value in the body (blood) of the testee. Thus, a rapid and convenient alcohol test method is provided to, when a user needs to accurately determine the alcohol value after drinking, receive and test the gas exhaled by the testee by means of the test device to rapidly obtain the alcohol value in the body (blood) of the testee, which helps the user accurately determine the alcohol consumption to make a correct determination.

Embodiment IV

Figure 6:
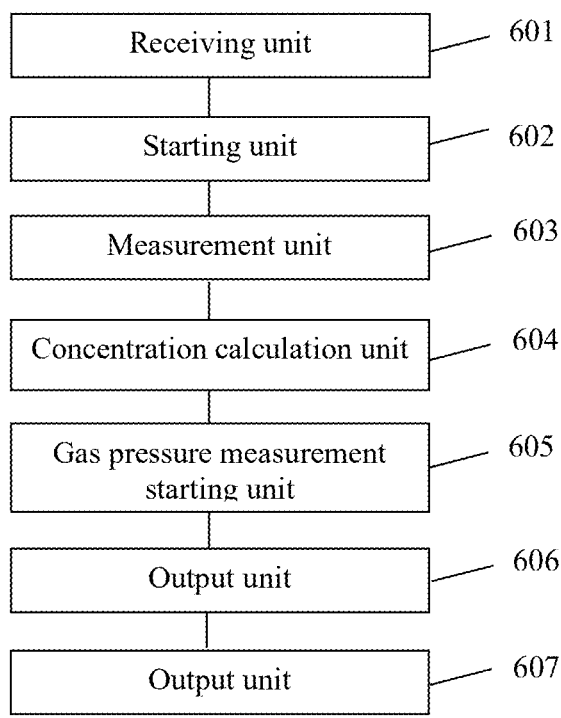
FIG. 6 is a structural view of an alcohol test apparatus provided according to a fourth embodiment of the present application.
Figure 7:
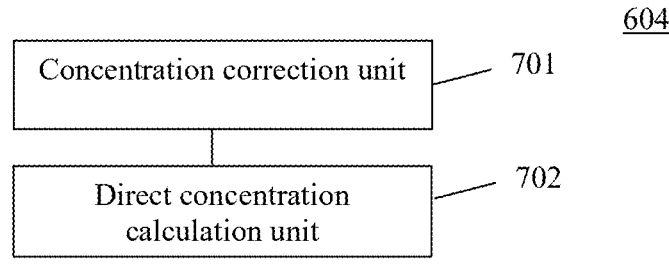
FIG. 7 is a structural view of a concentration calculation unit provided according to a fourth embodiment of the present application.

FIG. 6 shows a structural view of an alcohol test apparatus provided according to a fourth embodiment of the present application, and, for ease of illustration, only shows the parts related to the embodiment of the present application.

A receiving unit 601 is configured to receive gas exhaled by a testee from a gas channel.

In the specific implementation process, a gas inlet of a test device can receive the gas in the breath exhaled by the testee. Since the exhaled gas in the breath has a certain flow rate, the gas flow can rapidly enter the test device from the gas inlet of the test device, and the gas then enters the gas channel via the gas inlet and finally enters a measurement unit of the test device, realizing the function of receiving gas.

A starting unit 602 is configured to measure a gas pressure value of the exhaled gas, and start alcohol content measurement when the gas pressure value of the exhaled gas is greater than or equal to a first threshold.

In the specific implementation process, since the exhaled gas in the breath will enter air and be mixed with gas in the air, the gas flow rate will decrease during the mixing process, the lower the flow rate of the exhaled gas, the better it mixes with the gas in the air. When the exhaled gas in the breath is mixed with a large amount of the gas in the air due to too low flow rate of the exhaled gas or when the exhaled gas in the breath is too far away from the test device, the exhaled gas will be fully mixed with the gas in the air, which will eventually lead to serious deviations in the testing data. Therefore, in order to obtain accurate data, it is necessary to measure the gas pressure value of the exhaled gas, measure the gas pressure value of the gas exhaled into the test device, determine whether to start alcohol content measurement according to the gas pressure value, and start alcohol content measurement when the gas pressure value of the exhaled gas is greater than or equal to the set first threshold.

A measurement unit 603 is configured to measure an alcohol content in the gas according to the gas exhaled by the testee from the gas channel.

In the specific implementation process, after the test device receives the exhaled gas, the test device can test the exhaled gas entering the gas channel, and measure the alcohol content in the body of the testee according to the measurement of the alcohol content in the gas.

A concentration calculation unit 604 is configured to obtain a gas alcohol concentration value according to the measured alcohol content in the gas.

In the specific implementation process, when the alcohol content value of the gas in the breath exhaled by the testee is obtained, the alcohol concentration value of the gas can be calculated according to the gas alcohol value. The gas alcohol value is an alcohol content value of the gas exhaled by the testee, and the gas alcohol concentration value is an alcohol content value in the body (blood) of the testee. Since there is a certain proportional numerical relationship between the alcohol content value during the human breathing process and the alcohol content value in the body (blood), the alcohol concentration value in the body (blood) of the testee can be calculated when the gas alcohol value is obtained.

a gas pressure measurement starting unit 605 is configured to measure a gas pressure value of the exhaled gas, and determine a gas pressure range of the gas pressure value when the gas pressure value of the exhaled gas is greater than or equal to the first threshold.

In the specific implementation process, since the exhaled gas in the breath will enter air and be mixed with the gas in the air, the gas flow rate will decrease during the mixing process, the lower the flow rate of the exhaled gas, the better it mixes with the gas in the air. The exhaled gas in the breath at too low flow rate will be mixed with a large amount of the gas in the air, but the exhaled gas in the breath at a high flow rate may infer that the exhaled gas is in proximity and is difficult to mix with the gas in the air. Therefore, it is necessary to distinguish the gas at different flow rates from each other for accurate test. In this case, it is necessary to measure the gas pressure value of the exhaled gas, determine the gas pressure range of the gas pressure value when the gas pressure value of the exhaled gas is greater than or equal to the first threshold, and correct the value of the subsequent relevant data according to the measured gas pressure value.

An output unit 606 is configured to calculate an output alcohol concentration value according to the gas alcohol concentration value.

In the specific implementation process, when the gas alcohol concentration value is obtained, it is necessary to correct the specific alcohol concentration value or convert the corresponding relationship according to the actual situation. Since the alcohol concentration value of the gas in the breath exhaled by the testee and the alcohol concentration value in the body (blood) of the testee have a corresponding relationship that needs to be corrected, the value needs to be corrected again. After the gas pressure range of the gas pressure value is determined, the concentration calculation unit comprises a concentration correction unit 701 and a direct concentration calculation unit 702. a concentration correction unit configured to correct the gas alcohol concentration value when the gas pressure value of the exhaled gas is greater than or equal to the first threshold and less than or equal to a second threshold, and output the corrected value as the alcohol concentration value; and a direct concentration calculation unit configured to output the gas alcohol concentration value as the alcohol concentration value when the gas pressure value of the exhaled gas is greater than the second threshold. A calculation formula for correcting the gas alcohol concentration value is:

$$G_D = k * \left(1 + \frac{p_2 - p_x}{p_2 - p_1}\right) * G_X;$$

where $G_D$ is the corrected alcohol concentration, $G_x$ is the alcohol concentration, P2 is the second threshold, P1 is the first threshold, Px is the gas pressure value of the exhaled gas. The above calculation formula can be implemented by a correction calculation unit 607 of the apparatus. Preferably, the pressure value of the exhaled gas of P1 is between 150 Pa and 240 Pa, the pressure value of the exhaled gas of P2 is between 300 Pa and 500 Pa, and k is a measurement uncertainty coefficient. In the actual measurement, there will be certain uncertainty due to different sensors. The different curves marked by 1-5 or 1-12 in the figures represent different sample individuals. Through the experiment, it is found that there are large difference between different sample individuals, so that there will be some differences in the data calculated completely by using the formula. Thus, the k value coefficient is added, and the MCU will give different k values according to the actual sampled data during the sample preparation process to correct the entire algorithm curve. The setting of this uncertainty can be used to adjust the accuracy of the actual output. The schematic diagrams of k value are shown in FIGS. 3 and 4. FIG. 3 shows the k value of low concentration alcohol testing data graph, and FIG. 4 shows the k value of high concentration alcohol testing data graph. The data graphs of k value under different alcohol concentrations are shown. After correction, a more accurate final alcohol concentration value can be output.

According to the embodiment of the present application, an alcohol test apparatus is provided. With the apparatus, the alcohol test device is used to receive the gas exhaled by the testee from the gas channel, obtain the relevant data of the gas, and finally calculate the alcohol concentration value in the body (blood) of the testee. In order to obtain more accurate data, the test is only performed when the gas pressure reaches a certain value. In addition, in order to apply this test method to a small smart device or terminal device, it is also possible to measure the gas pressure without providing a mouthpiece and correct the data according to the gas pressure value, so that the hardware device for test can be a small smart device or terminal device without a mouthpiece. Thus, a rapid and convenient alcohol test method is provided to, when a user needs to accurately determine the alcohol value after drinking, receive and test the gas exhaled by the testee by means of the test device to rapidly obtain the alcohol value in the body (blood) of the testee, which helps the user accurately determine the alcohol consumption to make a correct determination.

The integrated unit, if implemented in the form of a software functional unit and sold or used as an independent product, can be stored in a computer-readable storage medium. On the basis of such understanding, the technical solutions of the present application, in essence, or the part that contributes to the prior art, or all or some of the technical solutions can be embodied in the form of a software product, which is stored in a storage medium and comprises several instructions to enable a computer device (which may be a personal computer, a server, a network device, etc.) to execute all or some of the steps of the method described in the embodiments of the present application. The aforementioned storage media include various media that can store program codes, such as a USB flash drive, a mobile hard disk, a read-only memory (ROM), a random access memory (RAM), a magnetic disk or an optical disk.

What are described above are only preferred embodiments of the present application but not intended to limit the present application, and any modifications, equivalent replacements, improvements, etc. made within the spirit and principle of the present application should be included within the scope of protection of the present application.

The invention claimed is:

1. An alcohol test method, comprising:
receiving gas exhaled by a testee from a gas channel;
measuring an alcohol content in the gas according to the gas exhaled by the testee from the gas channel;
obtaining a gas alcohol concentration value according to the measured alcohol content in the gas; and
calculating an output alcohol concentration value according to the gas alcohol concentration value, wherein a measurement uncertainty coefficient is employed in calculating the output alcohol concentration value to adjust an accuracy of the output alcohol concentration value, and the measurement uncertainty coefficient varies with different alcohol concentrations.

2. The method according to claim 1, further comprising, after receiving gas exhaled by a testee from a gas channel, measuring a gas pressure value of the exhaled gas, and starting alcohol content measurement when the gas pressure value of the exhaled gas is greater than or equal to a first threshold.

3. The method according to claim 1, further comprising, after obtaining a gas alcohol concentration value according to the measured alcohol content in the gas, measuring a gas pressure value of the exhaled gas, and determining a gas pressure range of the gas pressure value when the gas pressure value of the exhaled gas is greater than or equal to a first threshold.

4. The method according to claim 3, wherein calculating an output alcohol concentration value according to the gas alcohol concentration value specifically comprises:
correcting the gas alcohol concentration value when the gas pressure value of the exhaled gas is greater than or equal to the first threshold and less than or equal to a second threshold, and outputting the corrected value as the alcohol concentration value; and
outputting the gas alcohol concentration value as the alcohol concentration value when the gas pressure value of the exhaled gas is greater than the second threshold.

5. The method according to claim 4, wherein the step of correcting the gas alcohol concentration value comprises:
determining a corrected alcohol concentration based on the gas alcohol concentration, the first threshold, the second threshold, the gas pressure value of the exhaled gas, and the measurement uncertainty coefficient according to a relationship:

$$G_D = k * \left(1 + \frac{p_2 - p_x}{p_2 - p_1}\right) * G_X;$$

12 where $G_D$ is the corrected alcohol concentration, $G_x$ is the alcohol concentration, P2 is the second threshold, P1 is the first threshold, Px is the gas pressure value of the exhaled gas, and k is the measurement uncertainty coefficient.

6. An alcohol test apparatus, comprising:
a receiving unit configured to receive gas exhaled by a testee from a gas channel;
a measurement unit configured to measure an alcohol content in the gas according to the gas exhaled by the testee from the gas channel;
a concentration calculation unit configured to obtain a gas alcohol concentration value according to the measured alcohol content in the gas; and
an output unit configured to calculate an output alcohol concentration value according to the gas alcohol concentration value, wherein a measurement uncertainty coefficient is employed to adjust an accuracy of the output alcohol concentration value, and the measurement uncertainty coefficient varies with different alcohol concentrations.

7. The apparatus according to claim 6, further comprising:
a starting unit configured to measure a gas pressure value of the exhaled gas, and start alcohol content measurement when the gas pressure value of the exhaled gas is greater than or equal to a first threshold.

8. The apparatus according to claim 6, further comprising:
a gas pressure measurement starting unit configured to measure a gas pressure value of the exhaled gas and determine a gas pressure range of the gas pressure value when the gas pressure value of the exhaled gas is greater than or equal to the first threshold.

9. The apparatus according to claim 8, wherein the concentration calculation unit comprises:
a concentration correction unit configured to correct the gas alcohol concentration value when the gas pressure value of the exhaled gas is greater than or equal to the first threshold and less than or equal to a second threshold, and output the corrected value as the alcohol concentration value; and
a direct concentration calculation unit configured to output the gas alcohol concentration value as the alcohol concentration value when the gas pressure value of the exhaled gas is greater than the second threshold.

10. The apparatus according to claim 9, further comprising:
a correction calculation unit configured to correct and calculate the gas alcohol concentration value by a calculation formula of $$G_D = k * \left(1 + \frac{p_2 - p_x}{p_2 - p_1}\right) * G_X;$$

wherein $G_D$ is the corrected alcohol concentration, $G_x$ is the alcohol concentration, P2 is the second threshold, P1 is the first threshold, Px is the gas pressure value of the exhaled gas, and k is the measurement uncertainty coefficient.

* * * * *